US009402700B2

(12) United States Patent
Patel et al.

(10) Patent No.: US 9,402,700 B2
(45) Date of Patent: Aug. 2, 2016

(54) INTERDENTAL CLEANING DEVICE (75) Inventors: Madhusudan Patel, Somerset, NJ (US);
Thomas J. Boyd, Metuchen, NJ (US);
Eduardo J. Jimenez, Manalapan, NJ
(US); Sharon Kennedy, Randallstown,
MD (US)

(73) Assignee: COLGATE-PALMOLIVE COMPANY, New York, NY (US)

( * ) Notice: Subject to any disclaimer, the term of this patent is extended or adjusted under 35 U.S.C. 154(b) by 292 days.

(21) Appl. No.: 14/004,070

(22) PCT Filed: Mar. 9, 2011

(86) PCT No.: PCT/US2011/027740
§ 371 (c)(1),
(2), (4) Date: Sep. 9, 2013

(87) PCT Pub. No.: WO2012/121720
PCT Pub. Date: Sep. 13, 2012

(65) Prior Publication Data
US 2013/0340185 A1    Dec. 26, 2013

(51) Int. Cl.
*B43K 8/00* (2006.01)
*B43K 7/10* (2006.01)
*A61C 15/00* (2006.01)
*A46B 11/00* (2006.01)
*A46B 7/00* (2006.01)
*A46B 9/04* (2006.01)
(Continued)

(52) U.S. Cl.
CPC ............... *A61C 15/00* (2013.01); *A61C 19/063* (2013.01)

(58) Field of Classification Search
CPC ...... A61C 15/00; A61C 19/063; A46B 11/00; A46B 11/01; A46B 11/0082
USPC ............ 132/90; 15/104.93; 433/82; 401/116, 401/99, 196–198, 269, 284, 188 R, 199, 109
See application file for complete search history.

(56) References Cited

U.S. PATENT DOCUMENTS 1,798,081 A   3/1931   Gordyn, Jr. et al.
1,973,212 A   9/1934   Krueger
(Continued)

FOREIGN PATENT DOCUMENTS

CN   2256235 Y   6/1997
CN   2343878     10/1999
(Continued)

OTHER PUBLICATIONS

Anonymous, 2008, "Salviathymol N".
(Continued)

*Primary Examiner* — Mark A Laurenzi
*Assistant Examiner* — Thomas M Abebe (57) ABSTRACT An interdental cleaning device that delivers an oral care fluid to a cleaning element via capillary action. The invention can be an interdental cleaning device comprising: a housing forming an internal reservoir containing an oral care fluid; an applicator extending from the housing, the applicator comprising a stem and at least one cleaning element extending from the stem; and wherein the stem comprises a capillary material that extends into the reservoir to be in fluid communication with the oral care fluid so that the capillary material of the stem delivers the oral care fluid from the reservoir to the at least one cleaning element via capillary action.

19 Claims, 8 Drawing Sheets (51) Int. Cl.
   *A61C 17/02* (2006.01)
   *A46B 3/18* (2006.01)
   *A46B 5/02* (2006.01)
   *A46B 5/00* (2006.01)
   *A61C 19/06* (2006.01)

(56) References Cited

U.S. PATENT DOCUMENTS

| | | | |
|---|---|---|---|
| 2,416,684 A | 3/1947 | Fischer | |
| 2,573,201 A | 10/1951 | Kelley et al. | |
| 2,594,721 A | 4/1952 | Beebe | |
| 2,739,328 A | 3/1956 | Bernier | |
| 3,369,543 A | 2/1968 | Ronco | |
| 3,685,080 A | 8/1972 | Hubner | |
| 3,810,479 A | 5/1974 | Miles | |
| 3,902,510 A | 9/1975 | Roth | |
| 3,910,706 A | 10/1975 | Del Bon | |
| 3,936,200 A | 2/1976 | O'Rourke | |
| 3,937,582 A | 2/1976 | Del Bon | |
| 4,017,871 A * | 4/1977 | Hubbard | B43K 8/003 346/140.1 |
| 4,023,580 A | 5/1977 | Pieters | |
| 4,060,870 A | 12/1977 | Cannarella | |
| 4,088,412 A | 5/1978 | Del Bon | |
| 4,124,316 A | 11/1978 | O'Rourke | |
| 4,236,651 A | 12/1980 | Meyer et al. | |
| 4,304,245 A | 12/1981 | Lichfield | |
| 4,462,136 A | 7/1984 | Nakao et al. | |
| 4,509,541 A * | 4/1985 | Manciocchi, Jr. | A61C 15/02 132/322 |
| 4,521,128 A | 6/1985 | O'Neal | |
| 4,538,631 A | 9/1985 | Prince | |
| 4,543,679 A | 10/1985 | Rosofsky et al. | |
| 4,585,018 A | 4/1986 | O'Connor | |
| 4,691,404 A * | 9/1987 | Tarrson | A46B 3/18 15/144.1 |
| 4,716,035 A | 12/1987 | Sampathkumar | |
| 4,733,586 A | 3/1988 | Manusch et al. | |
| 4,753,249 A | 6/1988 | Muller | |
| 4,828,420 A | 5/1989 | Otsuka et al. | |
| 4,867,183 A | 9/1989 | Busch et al. | |
| 2,154,209 A | 8/1990 | Kohn | |
| 4,973,181 A | 11/1990 | Jankewitz | |
| 4,990,329 A | 2/1991 | Sampathkumar | |
| 5,000,193 A | 3/1991 | Heelis et al. | |
| 5,017,036 A | 5/1991 | Vidovic | |
| 5,029,358 A * | 7/1991 | Zimmerman | A61C 15/00 15/106 |
| 5,033,898 A | 7/1991 | Williams | |
| 5,062,728 A | 11/1991 | Kuo | |
| 5,066,155 A | 11/1991 | English et al. | |
| 5,088,627 A | 2/1992 | Musel | |
| 5,094,254 A | 3/1992 | Krueckel et al. | |
| 5,096,319 A | 3/1992 | Gueret | |
| 5,098,297 A | 3/1992 | Chari et al. | |
| 5,102,251 A | 4/1992 | Kaufmann | |
| D337,659 S | 7/1993 | Lacy | |
| 5,309,590 A | 5/1994 | Giuliani et al. | |
| 5,346,324 A | 9/1994 | Kuo | |
| 5,352,052 A | 10/1994 | Kaufmann | |
| 5,407,287 A | 4/1995 | Braun et al. | |
| 5,435,033 A * | 7/1995 | Millner | A61C 15/00 132/321 |
| 5,458,563 A | 10/1995 | Stewart | |
| 5,463,792 A | 11/1995 | Hogan et al. | |
| 5,476,384 A | 12/1995 | Giuliani et al. | |
| 5,488,751 A * | 2/1996 | Gekhter | A46B 5/00 132/321 |
| 5,490,529 A | 2/1996 | Fitjer | |
| 5,490,736 A | 2/1996 | Haber et al. | |
| 5,492,426 A | 2/1996 | Gueret | |
| 5,509,742 A | 4/1996 | Balzarini | |
| 5,578,023 A | 11/1996 | Schneider | |
| 5,611,687 A | 3/1997 | Wagner | |
| 5,700,146 A * | 12/1997 | Kucar | A61C 17/227 132/322 |
| 5,709,233 A * | 1/1998 | Boland | A61C 15/047 132/322 |
| 5,769,553 A | 6/1998 | Chaudhri et al. | |
| 5,829,976 A * | 11/1998 | Green | A61C 15/00 401/134 |
| 5,842,248 A | 12/1998 | van Grol et al. | |
| 5,865,195 A | 2/1999 | Carter | |
| 5,875,798 A | 3/1999 | Petrus | |
| 5,910,122 A | 6/1999 | D'Angelo | |
| 6,039,489 A | 3/2000 | Harman et al. | |
| 6,059,570 A | 5/2000 | Dragan | |
| 6,082,999 A | 7/2000 | Tcherny et al. | |
| 6,089,776 A | 7/2000 | Kaufmann | |
| 6,095,707 A | 8/2000 | Kaufmann | |
| 6,142,694 A | 11/2000 | Rivlin et al. | |
| 6,164,858 A | 12/2000 | Kaufmann | |
| 6,183,155 B1 * | 2/2001 | Kaufmann | B43K 8/04 401/198 |
| 6,203,320 B1 | 3/2001 | Williams et al. | |
| 6,205,611 B1 | 3/2001 | Vigil | |
| 6,206,600 B1 | 3/2001 | Rosenberg et al. | |
| 6,244,774 B1 | 6/2001 | Barosso et al. | |
| 6,244,777 B1 | 6/2001 | Reid | |
| 6,322,268 B1 | 11/2001 | Kaufmann et al. | |
| 6,325,626 B1 * | 12/2001 | Blass | A46B 3/18 132/321 |
| 6,345,405 B1 | 2/2002 | Brackin | |
| 6,371,674 B1 | 4/2002 | Lerner | |
| 6,378,529 B1 | 4/2002 | Clemente Marco | |
| 6,418,940 B1 | 7/2002 | Tcherny et al. | |
| 6,434,773 B1 | 8/2002 | Kuo | |
| D465,625 S | 11/2002 | Price | |
| 6,497,527 B2 | 12/2002 | Kaufmann | |
| 6,533,734 B1 | 3/2003 | Corley, III et al. | |
| RE38,150 E | 6/2003 | Greatbatch et al. | |
| 6,599,048 B2 | 7/2003 | Kuo | |
| 6,623,698 B2 | 9/2003 | Kuo | |
| 6,663,679 B1 | 12/2003 | Duncan | |
| 6,669,390 B1 | 12/2003 | Porter et al. | |
| 6,669,475 B2 | 12/2003 | Kandelman et al. | |
| 6,669,930 B1 | 12/2003 | Hoic et al. | |
| 6,770,266 B2 | 8/2004 | Santarpia, III et al. | |
| 6,802,097 B2 | 10/2004 | Hafliger et al. | |
| 6,817,803 B1 | 11/2004 | Ong et al. | |
| 6,895,629 B1 | 5/2005 | Wenzler | |
| 6,899,280 B2 | 5/2005 | Kotary et al. | |
| 6,902,337 B1 | 6/2005 | Kuo | |
| 6,932,603 B2 | 8/2005 | Han et al. | |
| 6,932,604 B2 | 8/2005 | Han et al. | |
| D510,482 S | 10/2005 | Jimenez | |
| 7,003,839 B2 | 2/2006 | Hafliger et al. | |
| 7,021,851 B1 | 4/2006 | King | |
| 7,025,521 B2 | 4/2006 | Tsaur | |
| 7,108,868 B2 | 9/2006 | Jia et al. | |
| 7,124,894 B1 | 10/2006 | Dobos | |
| 7,143,462 B2 | 12/2006 | Hohlbein | |
| 7,192,611 B2 | 3/2007 | Jia et al. | |
| 7,201,527 B2 | 4/2007 | Thorpe et al. | |
| 7,281,670 B2 | 10/2007 | Lakatos et al. | |
| 7,282,181 B2 | 10/2007 | Hudak et al. | |
| 7,303,143 B2 | 12/2007 | Davis et al. | |
| 7,311,456 B1 | 12/2007 | Neal | |
| 7,322,067 B2 | 1/2008 | Hohlbein | |
| 7,449,001 B2 | 11/2008 | Stoltz | |
| 7,478,960 B2 | 1/2009 | Glover | |
| 7,514,469 B2 | 4/2009 | Jia | |
| 7,596,974 B2 | 10/2009 | Smith et al. | |
| 7,699,608 B2 | 4/2010 | Han et al. | |
| 7,794,656 B2 | 9/2010 | Liang et al. | |
| 7,806,125 B2 | 10/2010 | Coopersmith | |
| 7,845,042 B2 | 12/2010 | Moskovich et al. | |
| 7,845,944 B2 | 12/2010 | DiGasbarro | |
| 2001/0002228 A1 | 5/2001 | Owens | |
| 2001/0024780 A1 * | 9/2001 | Antler | A61C 3/00 433/142 |
| 2002/0088473 A1 | 7/2002 | Fonseca et al. | |
| 2003/0045814 A1 | 3/2003 | Sangha | |

(56) References Cited

U.S. PATENT DOCUMENTS

| | | |
|---|---|---|
| 2003/0049327 A1 | 3/2003 | Zanone et al. |
| 2003/0053938 A1 | 3/2003 | Szeles |
| 2003/0086743 A1 | 5/2003 | Gruenbacher et al. |
| 2003/0120180 A1 | 6/2003 | Kaylor et al. |
| 2003/0157206 A1 | 8/2003 | Paek |
| 2003/0194678 A1 | 10/2003 | Viltro et al. |
| 2003/0224320 A1 | 12/2003 | Kandelman et al. |
| 2004/0020508 A1 | 2/2004 | Earl |
| 2004/0082878 A1 | 4/2004 | Baldwin et al. |
| 2004/0097834 A1 | 5/2004 | Stoltz |
| 2004/0182414 A1 | 9/2004 | Puskas |
| 2004/0220498 A1 | 11/2004 | Li et al. |
| 2004/0226575 A1 | 11/2004 | Hampton |
| 2004/0237226 A1 | 12/2004 | Hohlbein et al. |
| 2004/0255416 A1 | 12/2004 | Hohlbein et al. |
| 2005/0019087 A1 | 1/2005 | Tsaur |
| 2005/0026103 A1 | 2/2005 | Wasylucha |
| 2005/0091769 A1 | 5/2005 | Jimenez et al. |
| 2005/0115011 A1 | 6/2005 | Petit |
| 2005/0147461 A1 | 7/2005 | Glover |
| 2005/0201812 A1 | 9/2005 | Wong et al. |
| 2005/0217688 A1 | 10/2005 | Liu et al. |
| 2005/0218033 A1 | 10/2005 | Curtis |
| 2005/0220530 A1 | 10/2005 | Carmona |
| 2005/0221401 A1 | 10/2005 | Nomura et al. |
| 2005/0233279 A1 | 10/2005 | Zeh et al. |
| 2005/0244794 A1 | 11/2005 | Kemp et al. |
| 2006/0026784 A1 | 2/2006 | Moskovich et al. |
| 2006/0141421 A1 | 6/2006 | Braunecker et al. |
| 2006/0225744 A1 | 10/2006 | Braunecker et al. |
| 2006/0228163 A1 | 10/2006 | McSweeny |
| 2006/0280548 A1 | 12/2006 | Sharpe |
| 2007/0020032 A1 | 1/2007 | Abbas |
| 2007/0086831 A1 | 4/2007 | Wold |
| 2007/0101525 A1 | 5/2007 | Hohlbein |
| 2007/0151575 A1 | 7/2007 | DeMasi |
| 2007/0154863 A1 | 7/2007 | Cai et al. |
| 2007/0173738 A1 | 7/2007 | Stoltz |
| 2007/0183838 A1 | 8/2007 | Umar |
| 2007/0223988 A1 | 9/2007 | Gruenbacher et al. |
| 2007/0255177 A1 | 11/2007 | Pronovost |
| 2008/0014010 A1 | 1/2008 | Bartschi et al. |
| 2008/0034524 A1 | 2/2008 | Takahashi |
| 2008/0044791 A1 | 2/2008 | Tsurukawa et al. |
| 2008/0176183 A1* | 7/2008 | Gatzemeyer ......... A46B 11/001 433/82 |
| 2008/0201884 A1 | 8/2008 | Vazquez et al. |
| 2009/0012425 A1 | 1/2009 | Dodge et al. |
| 2009/0052972 A1 | 2/2009 | DellaCorte |
| 2009/0060622 A1 | 3/2009 | Lian et al. |
| 2009/0180826 A1 | 7/2009 | Guay |
| 2009/0205674 A1 | 8/2009 | Saloff et al. |
| 2009/0258326 A1 | 10/2009 | Al-Sulaiman et al. |
| 2009/0261179 A1 | 10/2009 | Hall |
| 2009/0317340 A1 | 12/2009 | Pak |
| 2009/0320226 A1 | 12/2009 | Robinson et al. |
| 2010/0223742 A1 | 9/2010 | Kang |
| 2010/0260532 A1* | 10/2010 | Tsai ..................... A45D 34/042 401/183 |
| 2010/0331725 A1 | 12/2010 | Libby et al. |

FOREIGN PATENT DOCUMENTS

| | | |
|---|---|---|
| DE | 3113450 | 10/1982 |
| DE | 3832520 | 4/1990 |
| DE | 4139141 | 6/1993 |
| DE | 10035214 | 2/2002 |
| DE | 202004008909 | 9/2004 |
| EP | 0092359 | 10/1983 |
| EP | 0097904 | 1/1984 |
| EP | 0244363 | 11/1987 |
| EP | 0373758 | 6/1990 |
| EP | 0631771 | 1/1995 |
| EP | 1053744 | 11/2000 |
| EP | 1095660 | 5/2001 |
| EP | 1270580 | 1/2003 |
| EP | 1639913 | 3/2006 |
| EP | 2174649 | 4/2010 |
| FR | 2452277 | 10/1980 |
| FR | 2777459 | 10/1999 |
| FR | 2923374 | 5/2009 |
| GB | 842965 | 8/1960 |
| GB | 2205280 | 12/1988 |
| GB | 2394653 | 5/2004 |
| GB | 2430146 | 3/2007 |
| JP | 1-097406 | 4/1989 |
| JP | 2-43099 | 2/1990 |
| JP | 2-152405 | 6/1990 |
| JP | 2-297498 | 12/1990 |
| JP | 9-215524 | 8/1997 |
| JP | 2003-019023 | 1/2003 |
| JP | 2003-250631 | 9/2003 |
| JP | 2004-108858 | 4/2004 |
| JP | 2005-257604 | 9/2005 |
| KR | 20-0183429 | 5/2000 |
| KR | 20030027985 | 4/2003 |
| KR | 100831148 | 5/2008 |
| NL | 9400631 | 12/1995 |
| RU | 2105519 | 2/1998 |
| RU | 15542 U1 | 10/2000 |
| RU | 2239342 | 11/2004 |
| TW | 200605814 | 2/2006 |
| WO | WO 92/10146 | 6/1992 |
| WO | WO 95/17159 | 6/1995 |
| WO | WO 99/05987 | 2/1999 |
| WO | WO 0115623 | 3/2001 |
| WO | WO 01/62082 | 8/2001 |
| WO | WO 03/000506 | 1/2003 |
| WO | WO 2004032785 | 4/2004 |
| WO | WO 2004/084752 | 10/2004 |
| WO | WO 2005/009352 | 2/2005 |
| WO | WO 2006/019289 | 2/2006 |
| WO | WO 2006/032367 | 3/2006 |
| WO | WO 2007/011552 | 1/2007 |
| WO | WO 2007/073917 | 7/2007 |
| WO | WO 2008/091935 | 7/2008 |
| WO | WO 2011/106017 | 9/2011 |

OTHER PUBLICATIONS

Anonymous, 2012, "Betaisodona-Mund-Antiseptikum".

Ciobanu et al., "Antimicrobial Mouthwash Concentrate—Inhibiting Cariogenic Buccal Flora Comprises Alcoholic Extract of Plants, Volatile Oils and Propolis Tincture," WPI Thomson AN 1993-203503.

Hyssopbrush, 2013, product description on CDM Supply website, http://cdmsupply.com/product_info.php?cPath=44&products_id=130.

International Search Report and Written Opinion in International Application No. PCT/US10/043825, mailed Apr. 28, 2011.

International Search Report and Written Opinion in International Application No. PCT/US11/027740, mailed Jan. 17, 2012.

International Search Report and Written opinion in International Application No. PCT/US2009/054582, mailed Aug. 3, 2010.

International Search Report and Written Opinion of corresponding International Application No. PCT/US2010/025605 dated Nov. 19, 2010.

International Search Report and Written Opinion of International Application No. PCT/US2008/051778 dated Dec. 12, 2008.

International Search Report and Written Opinion of International Application No. PCT/US2011/027042 mailed Nov. 28, 2011.

Office Action from the Taiwan Intellectual Property Office, dated Apr. 7, 2011, for corresponding Taiwan Patent Application No. 97102421.

Squirtbrush, 2013, product description on CDM Supply website, http://cdmsupply.com/product_info.php?cPath=42&products_id=109.

Written Opinion for PCT/US2010/025605 mailed on Mar. 1, 2012.

(56) References Cited

OTHER PUBLICATIONS

Written Opinion in International Application No. PCT/US11/027042, mailed Jul. 10, 2012.

Notice of Preliminary Rejection dated Oct. 20, 2014 in corresponding KR Application No. 7026424/2013. KR.
Official Action in corresponding RU Application No. 2013145082, filed Oct. 8, 2013. RU.

* cited by examiner

INTERDENTAL CLEANING DEVICE

CROSS-REFERENCE TO RELATED PATENT APPLICATIONS

The present application is a U.S. national stage application under 35 U.S.C. 371 of PCT Application No. PCT/US2011/027740, filed Mar. 9, 2011, the entirety of which is incorporated herein by reference.

FIELD OF THE INVENTION

The present invention relates to an oral care implement, and more particularly to an interdental cleaning device that delivers an oral care fluid via capillary action.

BACKGROUND OF THE INVENTION

Gum disease, also known as periodontitis or periodontal disease, is one of the most common dental problems that people suffer from. In its early stages, periodontal disease is not usually painful, which means that many people that have periodontitis do not even realize it. Research has shown that periodontal disease is an infection in the gums that is caused by the bacteria in plaque when plaque and bacteria build up on and between the teeth. To prevent periodontal disease, dentists recommend people to improve their dental hygiene such as by brushing and flossing regularly. In addition, mouthwash is also believed to be an effective method of removing plaque and bacteria from the teeth. By reducing the amount of plaque in a person's mouth, that person can reduce the amount of bacteria in the mouth and greatly reduce the chance of acquiring periodontal disease.

Brushing with a toothbrush is the most common method of removing plaque built-up on the teeth. However, due to the structure of toothbrushes, the bristles are unable to adequately remove all of the plaque from the areas between the teeth and around the gums. Specifically, the bristles of conventional toothbrushes are unable to easily penetrate from the buccal or lingual surfaces of the teeth at the interproximal teeth contact points. Consequently, these portions and interproximal regions of the teeth are typically not cleaned adequately and are prone to caries.

Therefore, flossing and the use of mouthwash have been considered the best secondary remedies and preventative methods for periodontal disease. However, flossing is a difficult activity for many people to conduct successfully. Specifically, many people have trouble properly holding the floss with enough strength so as to be able to force the floss between the teeth. Furthermore, even for people that are able to force the floss into the spaces between the teeth, the floss has been found to be inefficient, particularly with regards to the removal of stubborn plaque.

Therefore, a need exists for an interdental cleaning device that is easy to use and is able to effectively and adequately clean the spaces between adjacent teeth. Furthermore, a need exists for an interdental cleaning device that is able to apply an oral care fluid to the interdental areas while brushing/scrubbing the interdental areas. Additionally, a need exists for an interdental cleaning device that can provide targeted cleaning, sensitivity relief and other beneficial effects to hard to reach areas within the oral cavity.

BRIEF SUMMARY OF THE INVENTION

Exemplary embodiments of the invention are directed to an interdental cleaning device that comprises a reservoir and an applicator. In some exemplary embodiments, an oral care fluid disposed within the reservoir flows to the applicator via capillary action. The applicator comprises a stem and at least one cleaning element extending outwardly from the stem. In certain embodiments, the oral care fluid flows through the cleaning elements via capillary action. In certain other embodiments, the oral care fluid only flows through the stem via capillary action and is applied to a user's oral cavity by penetrating the spaces between the teeth with the applicator.

In one aspect, the invention can be an interdental cleaning device comprising: a housing forming an internal reservoir containing an oral care fluid; an applicator extending from the housing, the applicator comprising a stem and at least one cleaning element extending from the stem; and wherein the stem comprises a capillary material that extends into the reservoir to be in fluid communication with the oral care fluid so that the capillary material of the stem delivers the oral care fluid from the reservoir to the at least one cleaning element via capillary action.

The reservoir may be partially or completely filled with a mass of capillary material. In such embodiments, the mass of capillary material contains at least a portion of the oral care fluid. The mass of capillary material within the reservoir may be integrally formed with, or simply in contact with, the capillary material of the stem so that the oral care fluid can flow from the reservoir to the applicator.

In certain embodiments, the stem may be detachably coupled to the housing. In such embodiments, the stem comprises a plug portion and the mass of capillary material comprises a socket such that the plug portion can be disposed within the socket to enable the oral care fluid contained in the mass of capillary material to flow into the plug portion of the stem via capillary action.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE INVENTION

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of the exemplary embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "left," "right," "top," "bottom," "front" and "rear" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," "secured" and similar refer to a relationship wherein structures are secured or attached to one another either directly or indirectly through intervening structures, as well as both movable or rigid attachments or relationships, unless expressly described otherwise. Moreover, the features and benefits of the invention are described by reference to the exemplary embodiments illustrated herein. Accordingly, the invention expressly should not be limited to such exemplary embodiments, even if indicated as being preferred. The discussion herein describes and illustrates some possible non-limiting combinations of features that may exist alone or in other combinations of features. The scope of the invention is defined by the claims appended hereto.

Figure 1:
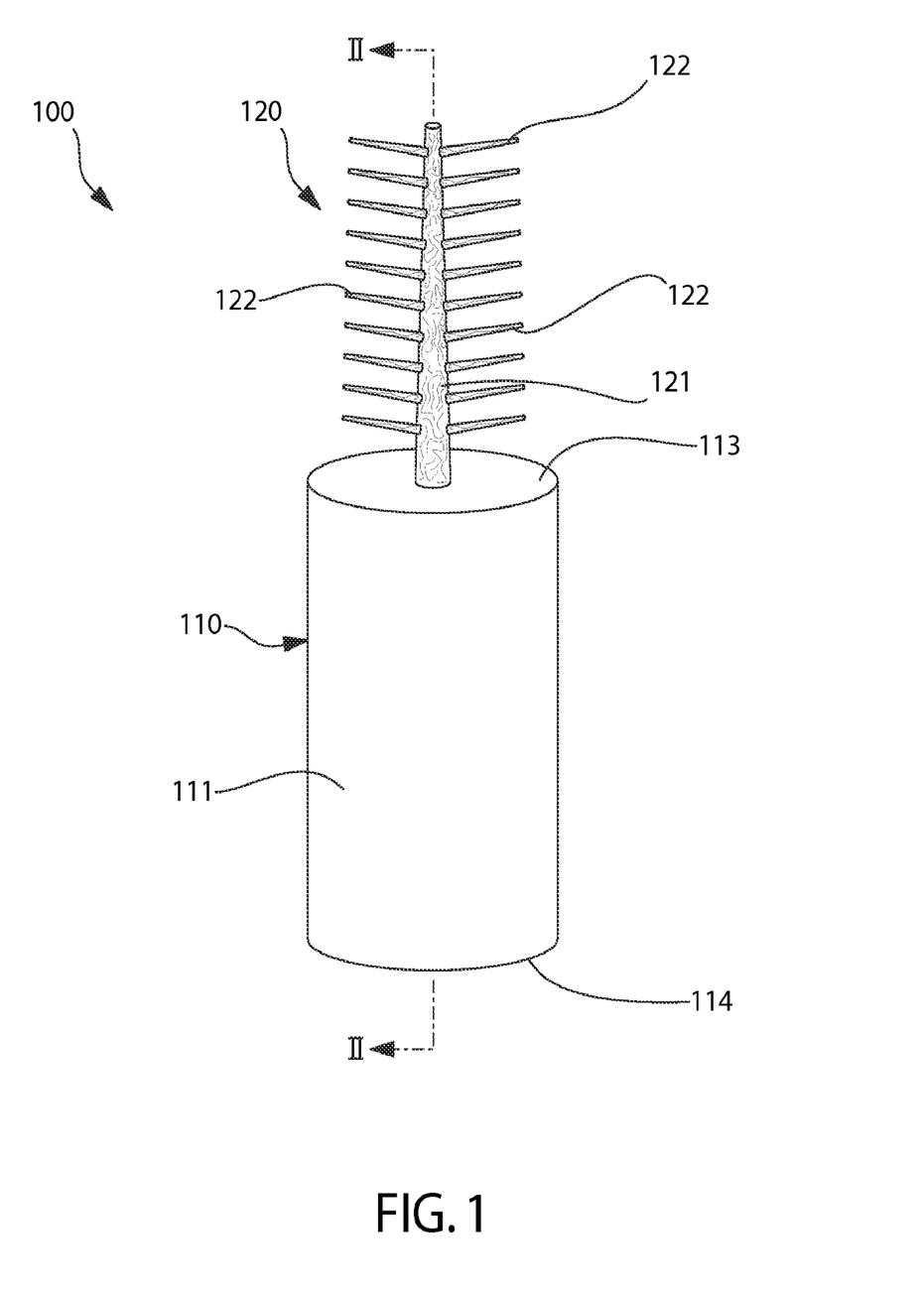
FIG. 1 is a front perspective view of an interdental cleaning device according to a first embodiment of the present invention.
Figure 2:
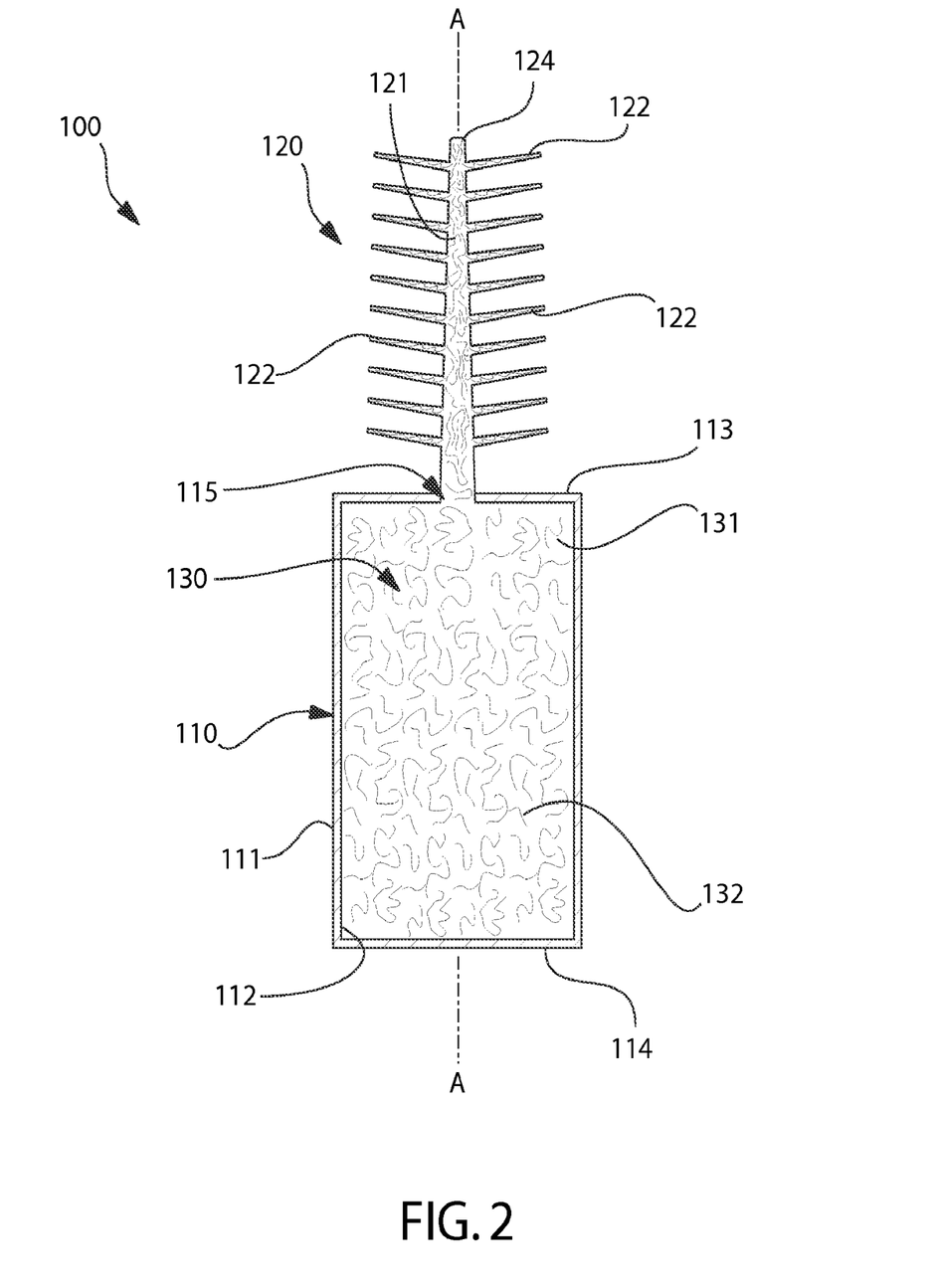
FIG. 2 is a cross-sectional view taken along the line II-II of FIG. 1 according to one embodiment of the present invention.

Referring to FIGS. 1 and 2, one embodiment of an interdental cleaning device 100 according to the present invention is illustrated. The interdental cleaning device 100 generally comprises a housing 110 and an applicator 120 extending from the housing 110. Although the housing 110 is illustrated generically as being cylindrical, the invention is not so limited and the housing 110 may take on any other shape including, without limitation, pyramidal, cubical, conical, spherical or the like. The housing 110 is sized and configured to comfortably fit within the hand of a user so that the user can easily manipulate the interdental cleaning device 100, and more particularly the applicator 120 of the interdental cleaning device 100, during a cleaning session. Thus, in certain embodiments the housing 110 acts as a handle for the interdental cleaning device 100. As such, in some embodiments an outer surface of the housing 110 can include grooves and elastomeric or rubber-like materials to facilitate gripping by a user and to prevent slippage.

The housing 110 has an outer surface 111, an inner surface 112, a top surface 113 and a bottom surface 114. The inner surface 112 of the housing 110 defines an internal reservoir 130. The internal reservoir 130 contains an oral care fluid 131 that provides oral health benefits to a user. For example, in certain embodiments the oral care fluid 131 is a mouthwash solution that cleans the oral surfaces when applied thereto and provides the user with breath freshening benefits. In other embodiments, the oral care fluid 131 can be a dentifrice or other tooth cleaning solution. Of course, the oral care fluid 131 is not to be in any way limiting of the present invention and may include fluids or agents that deliver therapeutic, cosmetic, experiential and/or sensorial benefits to a consumer during an interdental cleaning regimen. Specifically, the oral care fluid can be anti-sensitivity agents, fluoride, tartar protection agents, antibacterial agents, oxidative or whitening agents, enamel strengthening or repair agents, tooth erosion preventing agents, tooth sensitivity ingredients, gum health actives, nutritional ingredients, tartar control or anti-stain ingredients, enzymes, sensate ingredients, flavors or flavor ingredients, breath freshening ingredients, oral malodor reducing agents, anti-attachment agents or sealants, diagnostic solutions, occluding agents, dry mouth relief ingredients, catalysts to enhance the activity of any of these agents, colorants or aesthetic ingredients, arginine bicarbonate, chlorohexidine, triclosan, CPC, zinc oxide and combinations thereof.

The housing 110 is formed of a material that is able to fluidicly contain the oral care fluid 131 within the reservoir 130. Specifically, the housing 110 may be formed of a plastic material such as, for example, polyethylene terephthalate, high- or low-density polyethylene, polyvinyl chloride, polypropylene, polystyrene or polyamide. Of course, the invention is not limited to the housing 110 being formed of a plastic material and in other embodiments the housing 110 may be formed of a metal, rubber or any other material that is able to contain fluidic substances. As will be described below with reference to FIG. 6, in certain embodiments the housing 110 is formed of a material that is compressible as a result of force applied from a user squeezing the housing 110. Furthermore, the housing 110 may contain a clear window (not illustrated) to enable the user to see how much of the oral care fluid 131 remains in the reservoir 130. The clear window is not limited solely to being transparent but may also include translucent windows or windows that are colored, yet capable of being seen through. In certain other embodiments, the entire housing 110 may be formed of a clear material.

The interdental cleaning device 110 comprises a mass of capillary material 132 disposed within the reservoir 130. The mass of capillary material 132 contains at least a portion of the oral care fluid 131. The mass of capillary material 132 is formed of a capillary material that is suited to contain a fluidic material therein when the mass of capillary material 132 is subjected to or comes into contact with the fluidic material. For example, the mass of capillary material 132 can be a porous material, a fibrous material or a material comprising one or more capillary channels. In certain embodiments, such as is illustrated in FIG. 2, the mass of capillary material 132 fills a substantial entirety of the reservoir 130. When the mass of capillary material 132 is brought into contact with a liquid, such as the oral care fluid 131, the mass of capillary material 132 will begin absorbing the liquid at a rate which decreases over time as the mass of capillary material 132 becomes saturated with the liquid. The mass of capillary material 132 is in continuous contact with the oral care fluid 131 so that the mass of capillary material 132 can constantly deliver the oral care fluid 131 as will be described below.

The applicator 120 comprises a stem 121 and at least one cleaning element 122 extending from the stem 121. In the exemplary embodiment, the applicator 120 comprises a plurality of the cleaning elements 122 extending from the stem 121. However, the invention is not to be limited by the number or configuration of cleaning elements that extend from the stem 121. In the exemplary embodiment, the stem 121 extends from the housing 110 along a longitudinal axis A-A and the cleaning elements 122 extend transversely from the stem 121. The cleaning elements 122 extend from the stem 121 in a direction towards a distal end 124 of the stem 121 in a slightly angled manner. However, in certain other embodiments the cleaning elements 122 may extend from the stem 121 at an angle towards the housing 110 or the cleaning elements 122 may extend substantially perpendicularly from the stem 121. The particular angle that the cleaning elements 122 extend from the stem 121 is in no way limiting of the present invention, but may be altered as discussed above and as would be known to persons skilled in the art in order to achieve different cleaning benefits and mouth feels. In addition, while the cleaning elements 122 appear to extend at the same angle toward the distal end 124 in embodiment shown in FIGS. 1 and 2, in some embodiments, the cleaning elements 122 may extend at different angles.

The stem 121 comprises a capillary material and extends into the reservoir 130 through an opening 115 in the top surface 113 of the housing 110. In the embodiment illustrated in FIGS. 1 and 2, the stem 121 is formed entirely of the capillary material and the cleaning elements 122 are also formed entirely of the capillary material. In such embodiments, the capillary material of the cleaning elements 122 is of similar hardness, thickness, flexibility and shape as found in conventional interdental bristles. However, in certain other embodiments, only the stem 121 is formed of the capillary material and the cleaning elements 122 are formed of a non-capillary material, such as conventional interdental bristles as would be known to persons skilled in the art. The different materials and configurations that can form the stem 121 and cleaning elements 122 of the applicator 120 will be described in more detail below with reference to FIGS. 6-8.

Referring solely to FIG. 2, the capillary material of the stem 121 of the applicator 120 is integrally formed with the mass of capillary material 132 disposed in the reservoir 130. Thus, both the capillary material of the stem 121 and the mass of capillary material 132 are one of a porous material, a fibrous material, or a material comprising one or more capillary channels. More specifically, the capillary material of the stem 121 and the mass of capillary material 132 are formed from a porous wicking material, such as at least one of polyethylene, polypropylene, cellulose, wool, polyester, collagen, nylon and combinations thereof.

By forming the mass of capillary material 132 disposed within the reservoir 130 and the stem 121 of the applicator 120 out of a capillary material, the oral care fluid 131 within the reservoir 130 is drawn up through the mass of capillary material 132 and into the stem 121 via capillary action. The oral care fluid 131 is then delivered to the cleaning elements 122. It should be understood that the oral care fluid 131 can be delivered from the reservoir 130 to the cleaning elements 122 directly. Alternatively, the oral care fluid 131 can be delivered indirectly by drawing the oral care fluid 131 through the stem 121 and delivering it to the cleaning elements 122 via some other component. Furthermore, it should also be understood that capillary action includes the ability of liquid to flow against the pull of gravity by rising in a space, such as a thin tube, or through a porous material (and some non-porous materials, such as, without limitation, liquefied carbon fibre, as would be known to persons skilled in the art). The term "capillary action" may be used interchangeably herein with the term "wicking." Furthermore, a capillary material can be any material, including those described above and other materials now known to persons skilled in the art or later discovered, that facilitates the movement of liquid through the material against the pull of gravity. In certain embodiments, the oral care fluid is delivered from the reservoir 130 to the applicator 120 solely by capillary action. In other embodiments, the oral care fluid can be delivered from the reservoir 130 to the applicator by a combination of capillary action and mechanical action.

Although the stem 121 and mass of capillary material 132 are illustrated in FIG. 2 and described above as being integrally formed, in certain other embodiments, the capillary material of the stem 121 and the mass of capillary material 132 can be formed separately and coupled together during a later stage of the manufacturing process. The capillary material of the stem 121 and the mass of capillary material 132 can be made of a mixture of porous and/or fibrous materials which have a distribution of larger and smaller capillaries in order to achieve various storage capacities and rates of capillary flow as would be known to persons skilled in the art.

Furthermore, in certain embodiments the capillary action or wicking system, which includes the mass of capillary material 132 and the applicator 120, may be concentric and tubular in nature. In such an embodiment, the system comprises layers that can be conceptualized as onion layers. Each of the layers can provide different properties, compartments, mixing chambers and fluid release or absorbing characteristics as would be known to persons skilled in the art.

It should be understood that the rate and amount of fluid released from the interdental device 100 will be governed by the chemical and physical properties of the capillary material, the volume holding capacity of the reservoir 130 and the fluid properties as well as the pressure applied to or on the applicator 120 during use. The capillary material void volume, porosity, pore size, density, size and shape will also influence the desired fluid release rate characteristics. Each of these properties can be individually altered and changed in a manner that would be known to persons skilled in the art in order to achieve desired capillary material properties. Furthermore, the capillary material can be treated with food grade surfactants to change the hydrophobicities and/or hydrophilicities to provide further control over the amount and rate of fluid released.

The interdental cleaning device 100 may comprise a sufficient amount of the oral care fluid 131 in the reservoir 130 so that it can be used multiple times. Specifically, the interdental cleaning device 100 can be used until the reservoir 130 is empty and the mass of capillary material 132 and applicator 120 are dry and depleted of the oral care fluid 131. Alternatively, the interdental cleaning device 100 may only comprise enough oral care fluid 131 to be a single-use item.

In use, a user grips the housing 110 and positions the applicator 120 within the user's oral cavity. Specifically, the applicator 120, including the stem 121 and cleaning elements 122, is positioned in between adjacent teeth of the user in order to clean the interproximal/interdental tooth surfaces. The cleaning elements 122 provide an enhanced cleaning and scraping action to the interproximal/interdental tooth surfaces in order to remove plaque and bacteria. The applicator 120, which is formed at least partially of a capillary material as discussed above, will contain/store an amount of the oral care fluid 131. As the applicator 120 is pushed in between adjacent teeth, the contact between the capillary material and the tooth surfaces will put pressure on the capillary material and cause the oral care fluid 131 to be released from the capillary material. As such, the oral care fluid 131 is delivered onto the user's oral care surfaces, particularly the interproximal/interdental tooth surfaces to provide them with enhanced cleaning and other health benefits. As the oral care fluid 131 is released from the capillary material of the applicator 120, additional amounts of the oral care fluid 131 will continuously be absorbed by the capillary material of the applicator 120 from the reservoir 130.

Figure 3:
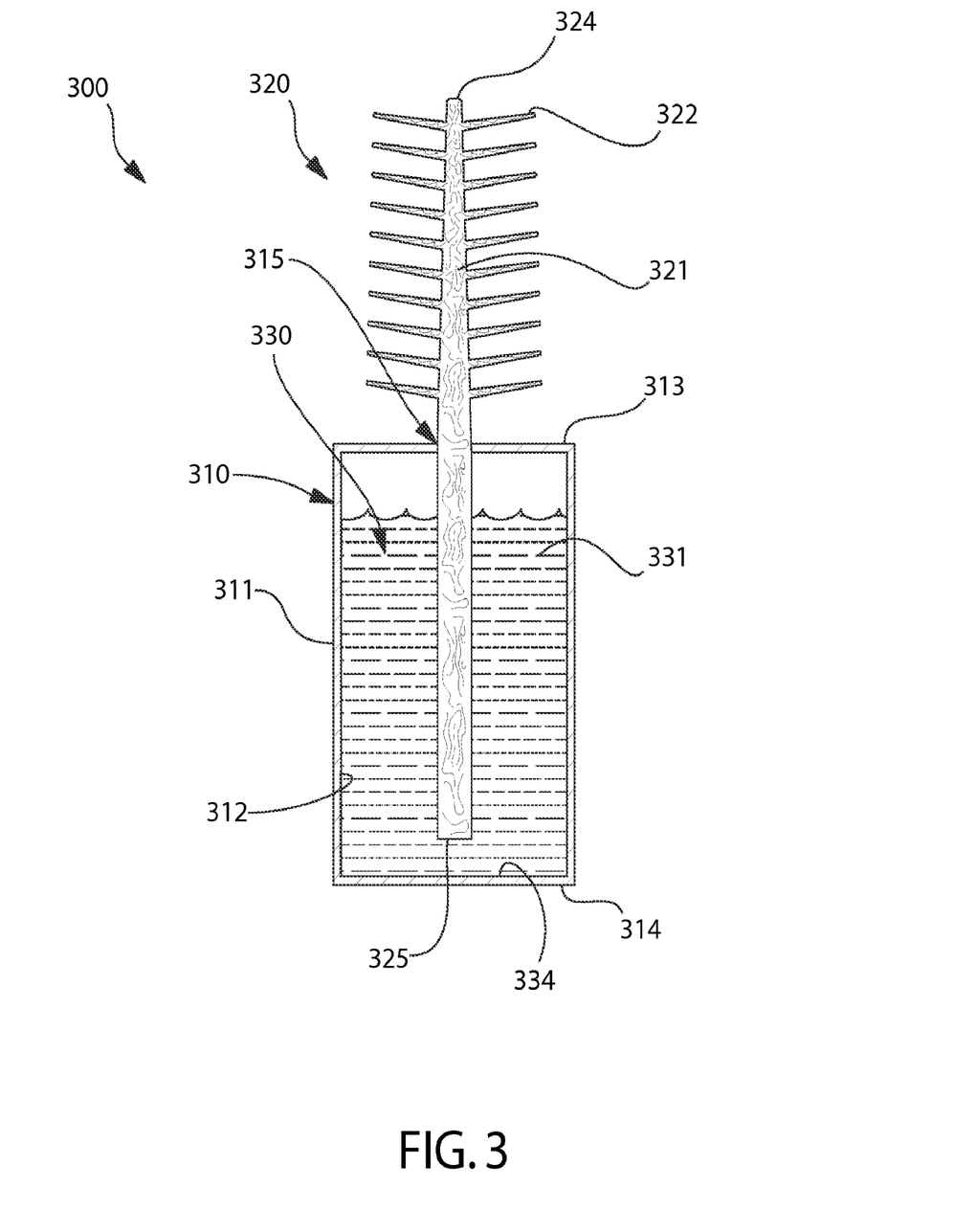
FIG. 3 is a cross-sectional view taken along the line II-II of FIG. 1 according to an alternative embodiment of the present invention.

Referring to FIG. 3, an interdental cleaning device 300 will be described. The external components of the interdental cleaning device 300 are the same as the components of the interdental cleaning device 100. Therefore, only those components of the interdental cleaning device 300 that are different from the interdental cleaning device 100 will be described below. Components of the interdental cleaning device 300 that are the same as or similar to components of the interdental cleaning device 100 will be numbered the same except the 300-series of numbers will be used.

The interdental cleaning device 300 comprises a housing 310 having an internal reservoir 330. The reservoir 330 contains an oral care fluid 331. However, unlike the interdental device 100, the reservoir 330 of the housing 310 comprises the oral care fluid 331 entirely in its liquid form. In other words, there is no capillary or other sponge-like material disposed within the reservoir 330 for absorbing and storing the oral care fluid 331 (with the exception of the capillary material of the stem of the applicator as will be described below).

The interdental device 300 comprises an applicator 320 having a stem 321 with cleaning elements 322 extending outwardly therefrom. The stem 321 of the applicator 320 extends into the reservoir 330 through an opening 315 in a top surface 313 of the housing 310. In the exemplary embodiment, the stem 321 extends into the reservoir 330 so that a proximal end 325 of the stem 321 is substantially near a floor 334 of the reservoir 330. In certain other embodiments, the proximal end 325 of the stem 321 extends all the way to the floor 334 of the reservoir 330 so that the proximal end 325 of the stem 321 makes contact with the floor 334 of the reservoir 330. In other embodiments, the proximal end 325 of the stem 321 extends half way to the floor 334 and the floor 334 may be movable towards the top surface 313 of the housing 310 as the oral care fluid 331 flows from the reservoir 330.

The stem 321 is formed of a capillary material. Thus, as the stem 321 comes into contact with the oral care fluid 331, the stem 321 absorbs the oral care fluid 331 and the oral care fluid 331 flows up through the stem 321 towards a distal end 324 of the stem 321. The stem 321 absorbs the oral care fluid 331 until the entire stem 321 from the proximal end 325 to the distal end 324 is saturated with the oral care fluid 331. As the interdental cleaning device 300 is used to clean in between a user's teeth in the manner discussed above, the oral care fluid 331 becomes expelled from the stem 321. As oral care fluid 331 is expelled from the stem 321, the stem 321 continues to absorb additional oral care fluid 331 from the reservoir 330 so as to remain saturated with the oral care fluid 331 until all of the oral care fluid 331 is soaked up by and contained within the stem 321 of the applicator 320.

The closer the proximal end 325 of the stem 321 is to the floor 334 of the reservoir 330, the more of the oral care fluid 331 that the stem 321 will be able to transfer via capillary action or wicking. In other words, the stem 321 is in direct contact with the oral care fluid 331 in order to absorb the oral care fluid 331. Thus, it is preferable that the stem 321 extend to the floor 334 of the reservoir 330 as described above. Regardless of how far into the reservoir 330 the stem 321 extends, the stem 321 is in continuous contact with the oral care fluid 331 so as to be able to constantly deliver the oral care fluid 331 as has been described herein.

The reservoir 330 of the interdental cleaning device 300 can be refillable. Specifically, the housing 310 may comprise a removable cover that can be detached from the housing 310 so that additional oral care fluid can be introduced into the reservoir 330. Alternatively, the interdental cleaning device 300 may include oral care fluid cartridges that are removable and replaceable. As such, when the oral care fluid 331 within the reservoir 330 has become depleted, the empty oral care fluid cartridge can be removed from the housing 310 and a new oral care fluid cartridge containing an oral care fluid can be coupled to the housing 310 in such a manner that the stem 321 of the applicator 320 is in contact with the oral care fluid. In this manner, not only can the oral care fluid 331 be replaced, but different oral care fluids can be used with the same housing 310 and applicator 320. In certain other embodiments, the housing 310 may include one or more openings that include one or more one-way valves. In these embodiments, additional oral care fluid can be introduced into the reservoir 330 via the one or more openings.

Figure 4:
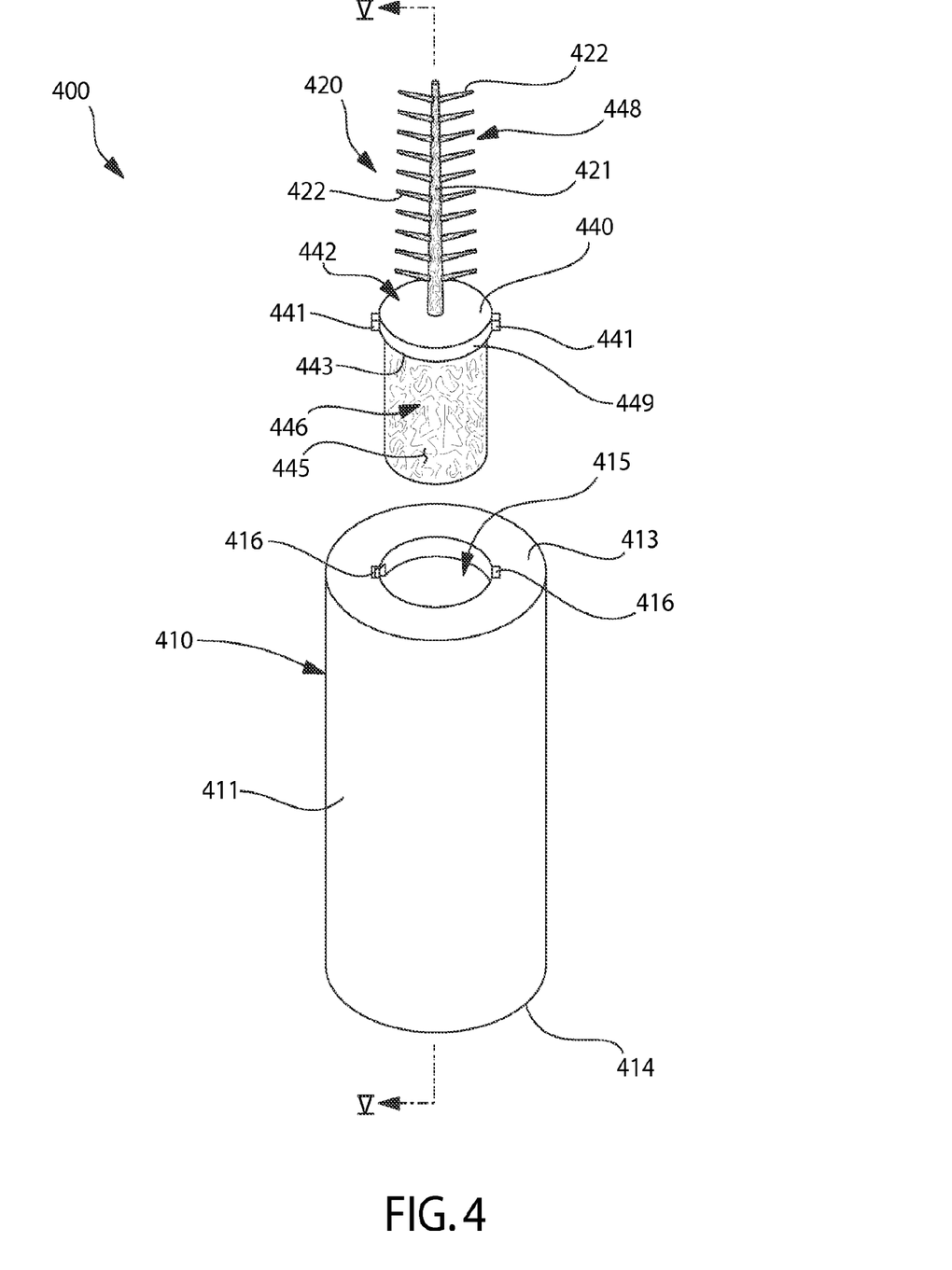
FIG. 4 is a front perspective view of an interdental cleaning device according to a second embodiment of the present invention.
Figure 5:
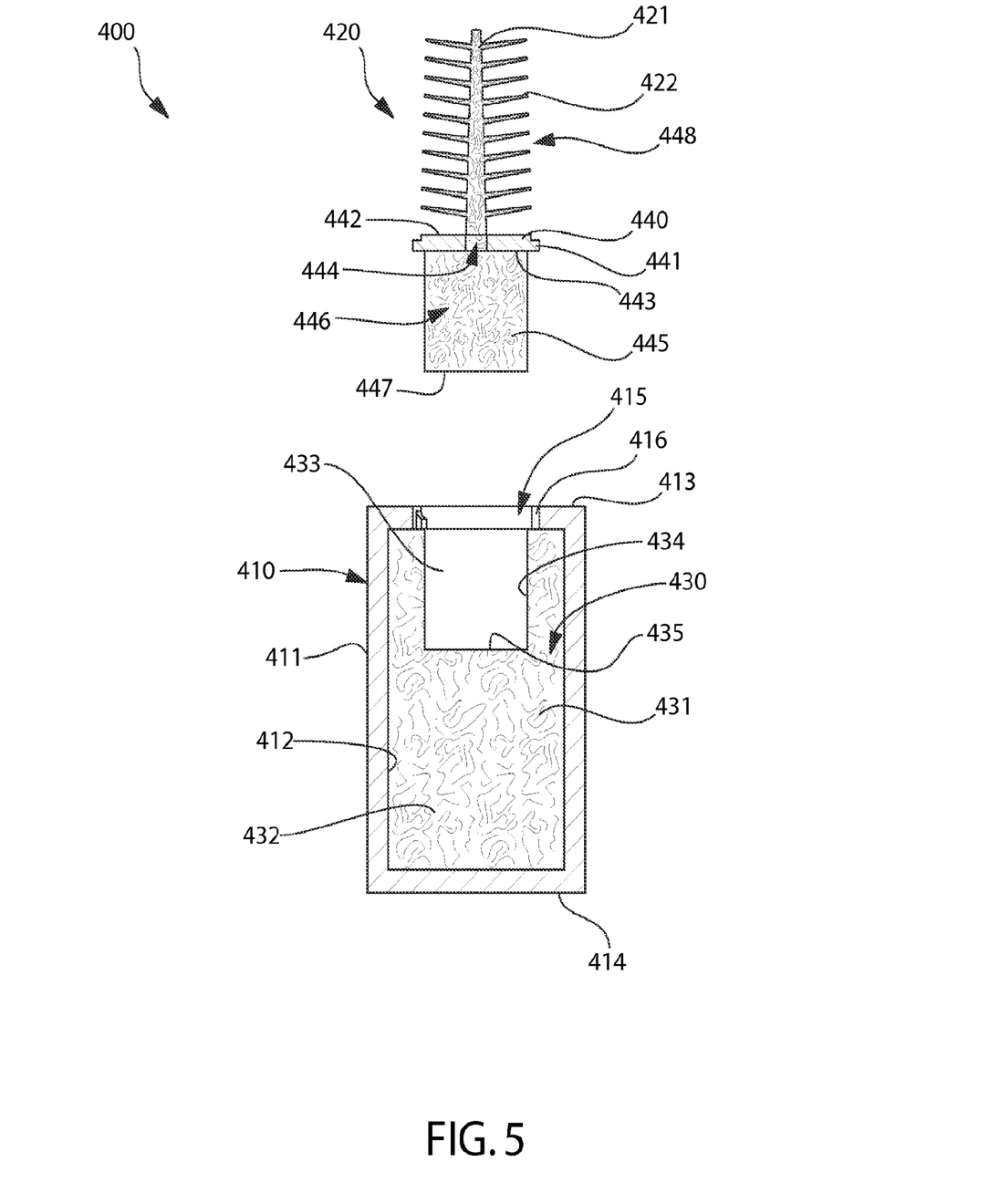
FIG. 5 is a cross-sectional view taken along the line V-V of FIG. 4.

Referring to FIGS. 4 and 5, another embodiment of an interdental cleaning device 400 is illustrated. Similar to the interdental cleaning device 100, the interdental cleaning device 400 comprises a housing 410 having an outer surface 411, an inner surface 412, a top surface 413 and a bottom surface 414. The top surface 413 of the housing 410 comprises an opening 415.

The housing 410 comprises an interior reservoir 430 defined by the inner surface 412. The reservoir 430 contains an oral care fluid 431 that provides health benefits to a user upon use, such as any of the oral care fluids described above with reference to FIGS. 1 and 2. A mass of capillary material 432 is disposed in the reservoir 430 and contains at least a portion of the oral care fluid 431. The mass of capillary material 432 is disposed within and fills a substantial entirety of the reservoir 430. However, the mass of capillary material 432 comprises a socket 433, which is a portion of the reservoir 430 that is devoid of the mass of capillary material 432.

The interdental cleaning device 400 also comprises an applicator 420 that includes a stem 421 and cleaning elements 422 extending from the stem 421. The applicator 420 is detachable from the housing 410 such that it can be coupled to the housing 410 during use and removed from the housing 410 when the interdental cleaning device 400 is not being used and for refilling the reservoir 430 with the oral care fluid 431 after depletion thereof. When the applicator 420 is detached from the housing 410, an additional amount of the oral care fluid 431 can be introduced into the reservoir 430 through the opening 415 for absorption by the mass of capillary material 432.

In the exemplary embodiment, the opening 415 is illustrated as being a circular opening in the top surface 413 of the housing 410. Of course, the invention is not to be limited by the size or shape of the opening 415. Therefore, in certain embodiments, the entire top surface 413 of the housing 410 may be open as would be understood by persons skilled in the art.

The applicator 420 also comprises a closure plate 440. Although the closure plate 440 is illustrated as being a circular plate, the invention is not so limited and the closure plate 440 may take on any other shape as would be known to persons skilled in the art. In some embodiments, the shape of the closure plate 440 correspond to the shape of the opening 415 in the top surface 413 of the housing 410 so that the closure plate 440 can close the opening 415. Furthermore, the closure plate 440 is preferably formed of a material that is able to fluidicly contain the oral care fluid 431 within the reservoir 430. The closure plate 440 may be made of the same material as the housing 410 or may be formed of a different material that is also capable of containing the oral care fluid 431.

The closure plate 440 is sized and configured so as to close the opening 415. Specifically, the closure plate 440 comprises two protrusions 441 positioned 180 degrees apart along a periphery 449 of the closure plate 440. Furthermore, the top surface 413 of the housing 410 has two notches 416 that are spaced 180 degrees apart. Thus, when the closure plate 440 is positioned over the opening 415, the protrusions 441 properly fit within the notches 416. Once the protrusions 441 are positioned within the notches 416, the closure plate 440 can be rotated relative to the housing 410 so that the cover plate 440 will be securely attached to the housing 410. Of course, any other method of attaching the cover plate 440 to the housing 410 as would be known to persons skilled in the art may be used. For example, the cover plate 440 may attach to the housing 410 by snap fit, interference fit, hook and loop fasteners, snaps or the like.

The closure plate 440 comprises a first side 442, a second side 443 and an aperture 444 extending through the closure plate 440 from the first side 442 to the second side 443. The stem 421 of the applicator 420 extends through the aperture 444 in the closure plate 440 and extends outwardly from both the first and second sides 442, 443 of the closure plate 440. Specifically, the stem 421 comprises a plug portion 445 that is located on and extends from the second side 443 of the closure plate 440 and a cleaning element-bearing portion 448 that extends from the first side 442 of the closure plate 440. The plug portion 445 and cleaning element-bearing portion 448 of the stem 421 can be integrally formed as a single unit or separately formed and connected at a later step in the manufacturing process. Furthermore, the plug portion 445 and the cleaning element-bearing portion 448 can be formed of the same material or of different materials as will be described in more detail below.

The plug portion 445 is sized and configured to correspond with the size and configuration of the socket 433. In the exemplary embodiment, the plug portion 445 is cylindrical shaped and the shape of the socket 433 corresponds to the cylindrical shape of the plug portion 445. Of course, the invention is not so limited and the plug portion 445 and socket 433 can take on any other shape as would be known to persons skilled in the art.

When the closure plate 440 is detachably coupled to the housing 410 as described above, the plug portion 445 fits snugly within the socket 433. When the plug portion 445 is disposed within the socket 433, an outer surface 446 of the plug portion 445 is in contact with an inner surface 434 of the mass of capillary material 432 that defines the socket 433. Furthermore, a bottom surface 447 of the plug portion 445 is in contact with a floor 435 of the socket 433. The contact between the plug portion 445 and the mass of capillary material 432 enhances the capillary flow of the oral care fluid 431 from the mass of capillary material 432 to the plug portion 445 and eventually to the stem 421 and cleaning elements 421 of the applicator 420. In some embodiments, the plug portion 445 may comprise a cap that is detachably coupled to the plug portion 445. The cap encloses plug portion 445 and protects the plug portion 445 against debris and dust so as to maintain plug portion 445 in a hygienic manner when plug portion 445 is not disposed within the socket 433.

The entirety of the stem 421 including the plug portion 445 and the cleaning element-bearing portion 448 is formed of a capillary material. Additionally, as discussed above, the mass of capillary material 432 is formed of a capillary material. In certain embodiments, the entirety of the stem 421 and the mass of capillary material 432 are formed of the same capillary material. However, in other embodiments, the mass of capillary material 432 is formed of a first capillary material, the plug portion 445 is formed of a second capillary material and the cleaning element-bearing portion 448 of the stem 421 is formed of a third capillary material. The pore sizes of the first, second and third capillary materials may decrease or increase from the first capillary material to the third capillary material in order to change the storage capacity of the various components and the rate of flow of the oral care fluid 431 from the reservoir 430 to the applicator 420 as discussed in detail above.

Figure 6:
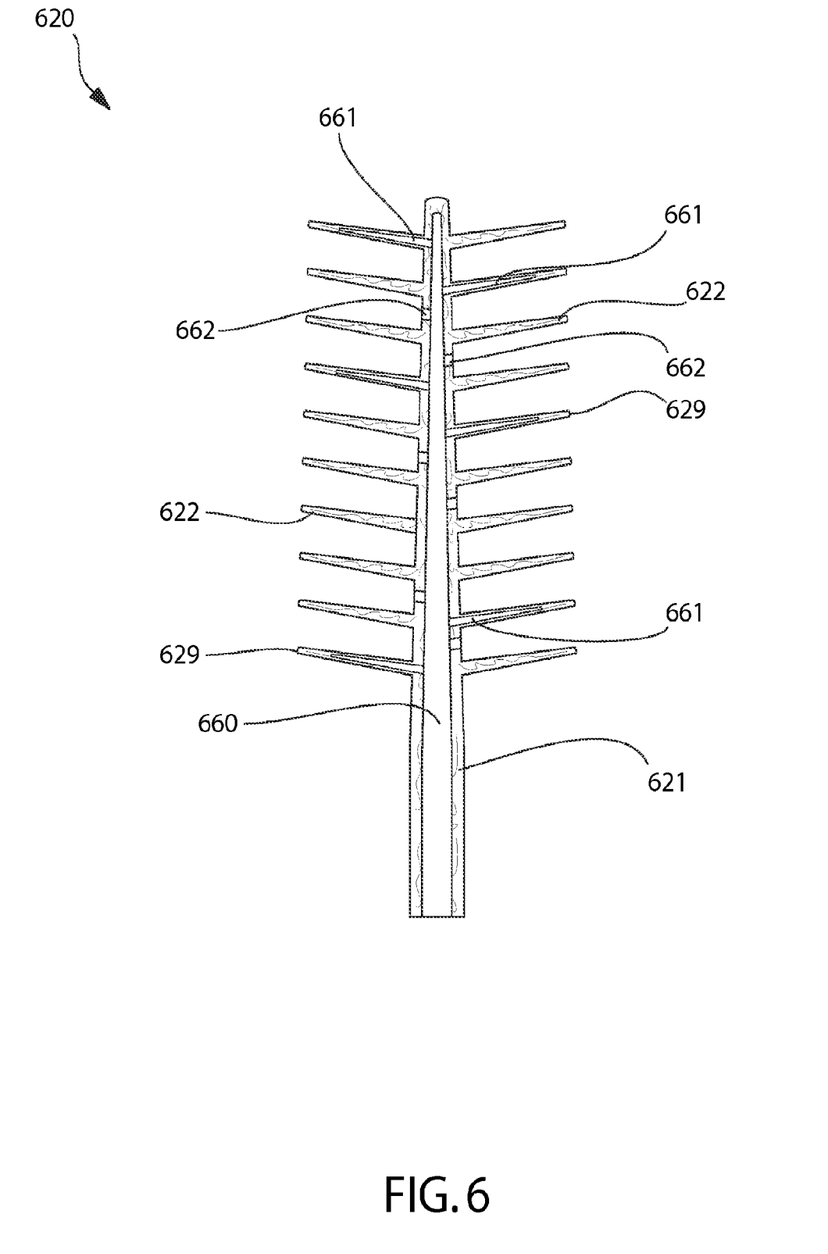
FIG. 6 is a front view of an applicator for interdental cleaning having channels therein.

Referring to FIG. 6, an applicator 620 according to an embodiment of the present invention is illustrated. The applicator 620 can be used with any of the interdental cleaning devices 100, 300, 400 instead of the applicators 120, 320, 420 discussed above. The applicator 620 comprises a stem 621 and a plurality of cleaning elements 622 extending outwardly from the stem 621. The stem 621 of the applicator 620 comprises a capillary channel 660. Although the stem 621 is illustrated as having only one capillary channel 660, in certain other embodiments the stem 621 can comprise more than one capillary channel 660. For example, the stem 621 can have a first capillary channel for distributing the oral care fluid to the cleaning elements 622 on the right side of the stem 621 and a second capillary channel for distributing the oral care fluid to the cleaning elements 622 on the left side of the stem 621.

Some of the cleaning elements 622 of the applicator 620 also have a capillary channel 661. Of course, in certain other embodiments, all of the cleaning elements 622 may have a capillary channel 661. The capillary channels 661 of the cleaning elements 622 extend from the capillary channel 660 of the stem 621 to a distal end 629 of the cleaning elements 622. The capillary channels 661 of the cleaning elements 622 are in fluid communication with the capillary channel 660 of the stem 621. This promotes the capillary flow of the oral care fluid from the stem 621 through the cleaning elements 622. By having the capillary channels 661 of the cleaning elements 622 extend to the distal ends 629 of the cleaning elements 622, the oral care fluid is able to flow through the entirety of the cleaning elements 622 for a more uniform and effective cleaning. When the applicator 620 is used with the interdental cleaning device 100, the capillary channels 660, 661 facilitates the flow of the oral care fluid 131 from the reservoir 130 to the cleaning elements 622 via capillary action.

Additional capillary channels 662 extend from the capillary channel 660 between adjacent cleaning elements 622. These additional capillary channels 662 further promote the capillary flow of the oral care fluid and the distribution of the oral care fluid to a user's oral cavity.

The capillary channels 660, 661, 662 are grooved into the stem 621 and cleaning elements 622 to facilitate the flow of an oral care fluid to the distal ends 629 of the cleaning elements 622. The widths of the capillary channels 660, 661, 662 can be varied to govern the rate of flow delivery and to enable the use of oral care fluids having various viscosities.

Similarly to the applicators 120, 320, 420 discussed above, the stem 621 and cleaning elements 622 of the applicator 620 may be formed entirely of a capillary material. In such embodiments, the cleaning elements 622 can be integrally formed with the stem 621. Of course, in other embodiments the applicator 620 including the stem 621 and cleaning elements 622 can be formed of a non-capillary material and the oral care fluid can be transported from the reservoir to the applicator 620 via capillary action through the capillary channels 660, 661, 662 only.

When using the applicator 620, it can be preferable to have a housing that is compressible or squeezable by a user. As such, a user will be able to force an oral care fluid out of the reservoir and into the capillary channels 660, 661, 662 discussed above to further facilitate the delivery of the fluids to a user's oral cavity. However, in certain embodiments, a pump or other suitable mechanism can be included in the interdental cleaning devices 100, 300, 400 to facilitate the delivery of the oral care fluid out of the reservoir and into the capillary channels 660, 661, 662. Thus, in these embodiments, the housing may not be compressible or squeezable.

Figure 7:
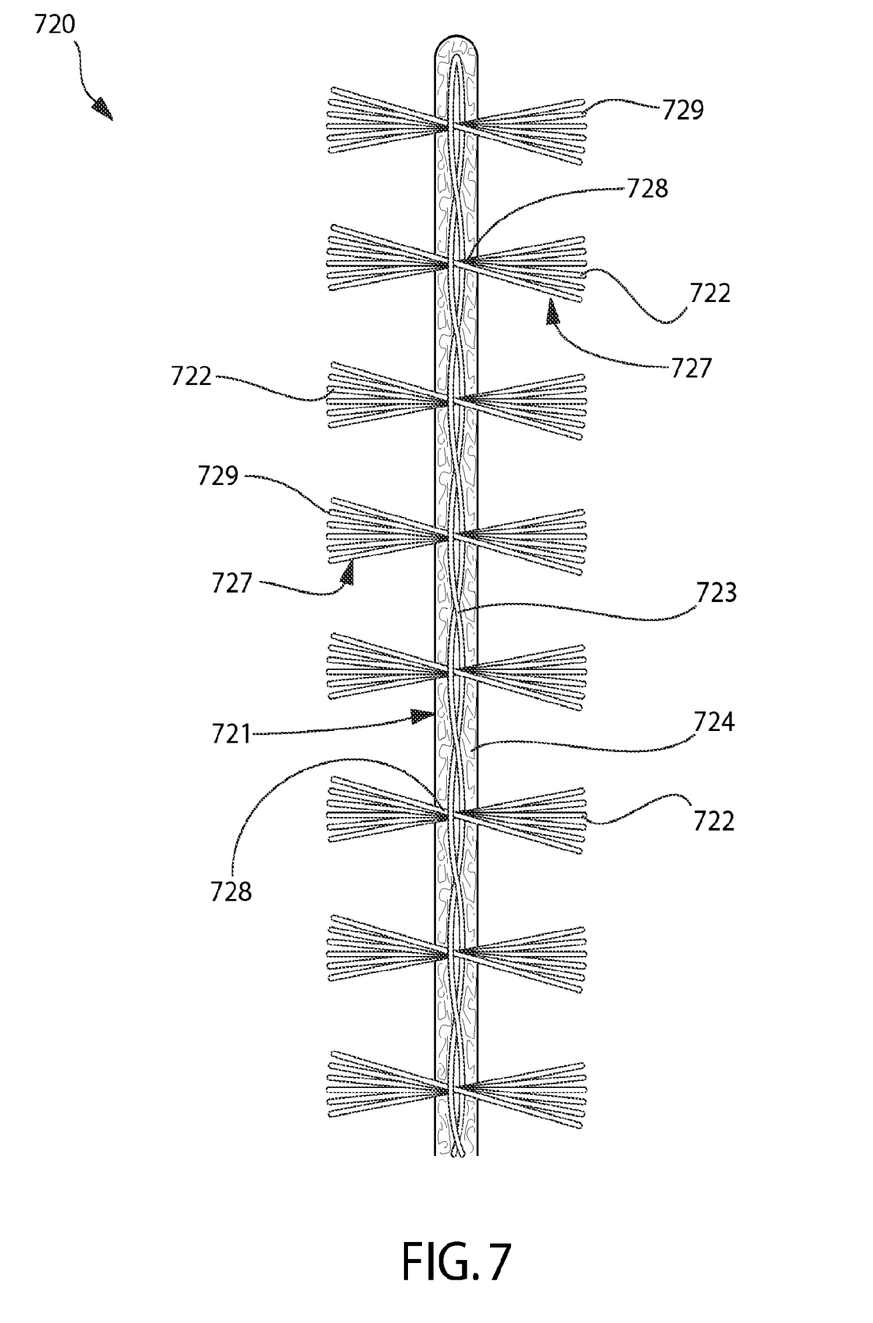
FIG. 7 is a front view of an applicator for interdental cleaning having a stem formed of a core that is disposed within a capillary material.

Referring to FIG. 7, an applicator 720 in accordance with another embodiment of the invention is illustrated. The applicator 720 comprises a stem 721 and cleaning elements 722 extending from the stem 721. The stem 721 comprises a core 723 and a capillary material 724. The core 723 is disposed or encased within the capillary material 724. The core 723 may be formed of a bendable wire that is bent in half to form a U-shape, and then twisted together. The cleaning elements 722 are preferably bristles, such as nylon bristles, that are attached to and extend from the core 723. The bristles 722 may be securely attached to the core 723 such as by welding or may be integrally formed with the core 723. Alternatively, as illustrated in FIG. 7, a portion 728 of the bristles 722 may be encased or disposed within the capillary material 724 while another portion 727 of the bristles 722, which is intended to engage a user's oral cavity and includes a distal end 729 of the bristles 722, protrudes from the capillary material 724. When in use, the capillary material 724 of the applicator 720 will absorb the oral care fluid from the reservoir and draw up and store the oral care fluid. When the applicator 720 is forced through the spaces between a user's teeth, the oral care fluid will be expelled from the capillary material 724 and deposited on a user's teeth to provide health benefits to the user.

It should be understood that in certain other embodiments, the core 723 can be formed of a capillary material and it can be disposed in or wrapped by a non-capillary material, such as a wire. In such embodiments, the core 723 will draw up the oral care fluid from the reservoir via capillary action. In such an embodiment, the wire that wraps the core 723 can be formed integrally with the bristles 722.

Figure 8:
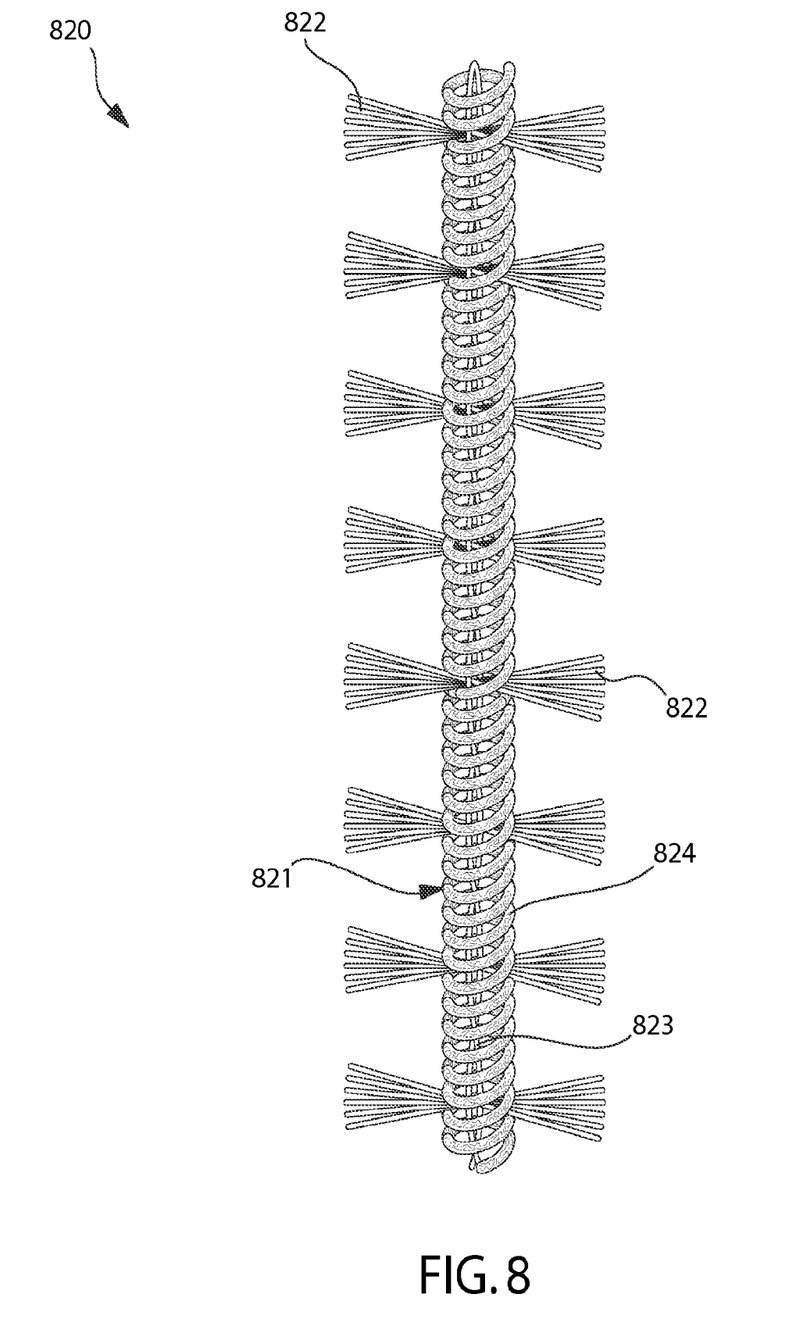
FIG. 8 is a front view of an applicator for interdental cleaning having a stem formed of a core that is wrapped or intertwined within a capillary material.

FIG. 8 illustrates an alternative embodiment of an applicator 820 that is similar to the applicator 720 illustrated in FIG. 7. The applicator 820 also comprises a stem 821 and cleaning elements 822 extending therefrom. The stem comprises a core 823, such as a bendable wire, that is disposed within a capillary material 824. However, in FIG. 8, the capillary material 824 does not entirely encase the core 823. Rather, the capillary material 824 of the applicator 820 wraps or is intertwined around the core 823, such as in the helical configuration illustrated.

It should be understood that in any of the embodiments described above, the interdental device 100, 300, 400 may also comprise a cap that is detachably coupled to the housing. The cap encloses the applicator and protects the applicator against debris and dust so as to maintain the applicator in a hygienic manner.

In some embodiments, the interdental devices 100, 300, 400 may be used to collect oral fluid for oral and systemic health diagnosis. In such embodiments, the interdental devices 100, 300, 400 will not have any oral care fluids disposed in a reservoir. Rather, the capillary materials described in detail above will be used to collect saliva, gingival crevicular fluid, bacteria, oral tissue debris and cells between the teeth and gum line for testing and diagnosis of any oral health problems. Thus, the capillary materials in such embodiments will be used to absorb and collect oral fluid for health diagnoses rather than containing oral care fluids and delivering the oral care fluids to the oral cavity to provide health benefits.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

While the foregoing description and drawings represent the exemplary embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, sizes, and with other elements, materials, and components, without departing from the spirit or essential characteristics thereof. One skilled in the art will appreciate that the invention may be used with many modifications of structure, arrangement, proportions, sizes, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being defined by the appended claims, and not limited to the foregoing description or embodiments.

What is claimed is:

1. An interdental cleaning device comprising:
a housing forming an internal reservoir containing an oral care fluid;
a mass of capillary material disposed in the reservoir and containing at least a portion of the oral care fluid;
an applicator extending from the mass of capillary material, the applicator comprising a stem extending along a longitudinal axis and a plurality of cleaning elements extending from the stem in opposing directions transverse to the longitudinal axis, and wherein an entirety of the stem that extends beyond a top surface of the housing to a distal end of the stem is exposed; and
wherein the stem comprises a capillary material that extends into the reservoir to be in fluid communication with the oral care fluid, and wherein the plurality of cleaning elements are integrally formed with the stem and constructed of the capillary material so that the capillary material of the stem delivers the oral care fluid from the reservoir to the plurality of cleaning elements via capillary action.

2. The interdental cleaning device according to claim 1 wherein the housing is formed of a material that fluidicly contains the oral care fluid within the reservoir.

3. The interdental cleaning device according to claim 1 wherein the mass of capillary material fills a substantial entirety of the reservoir.

4. The interdental cleaning device according to claim 1 wherein the mass of capillary material has a first pore size and the stem has a second pore size, the first pore size being greater than the second pore size.

5. The interdental cleaning device according to claim 1 wherein the capillary material of the stem is integrally formed with the mass of capillary material disposed in the reservoir.

6. The interdental cleaning device according to claim 1 wherein the capillary material of the stem and the mass of capillary material disposed in the reservoir are a porous material, a fibrous material, or a material comprising one or more capillary channels.

7. The interdental cleaning device according to claim 6 wherein the capillary material of the stem and the mass of capillary material disposed in the reservoir are selected from the group consisting of polyethylene, polypropylene, cellulose, wool, polyester, collagen, nylon and combinations thereof.

8. The interdental cleaning device according to claim 1 wherein the applicator is detachably coupled to the housing.

9. The interdental cleaning device according to claim 8 further comprising the stem comprising a plug portion formed of the capillary material, the mass of capillary material disposed in the reservoir comprising a socket, the plug portion disposed within the socket so that the oral care fluid contained in the mass of capillary material can flow into the plug portion of the stem via capillary action.

10. The interdental cleaning device according to claim 9 wherein the applicator comprises a closure plate through which the stem extends, the plug portion of the stem located on a first side of the closure plate and the plurality of cleaning elements disposed on a second side of the closure plate opposite the first side, the closure plate closing an opening in the housing when the applicator is detachably coupled to the housing, and the closure plate constructed of a material that fluidicly contains the oral care fluid within the reservoir.

11. The interdental cleaning device according to claim 8 wherein the applicator comprises a closure plate, the stem of the applicator extending through the closure plate, and wherein the closure plate closes an opening in the housing when the applicator is detachably coupled to the housing.

12. The interdental cleaning device according to claim 1 wherein the stem and the plurality of cleaning elements are constructed entirely of the capillary material.

13. The interdental cleaning device according to claim 1 wherein the stem comprises one or more capillary channels for flowing the oral care fluid from the reservoir to the plurality of cleaning elements via capillary action.

14. The interdental cleaning device according to claim 13 wherein the plurality of cleaning elements comprises a capillary channel in fluid communication with the one or more capillary channels of the stem.

15. The interdental cleaning device according to claim 1 wherein the stem comprises a core element disposed within the capillary material of the stem.

16. The interdental cleaning device according to claim 15 further comprising bristles secured to the core element and protruding from the capillary material.

17. The interdental cleaning device according to claim 15 wherein the core element is encased in the capillary material of the stem.

18. The interdental cleaning device according to claim 15 wherein the capillary material of the stem wraps around or is intertwined with the core element.

19. The interdental cleaning device according to claim 1 further comprising a cap that is detachably coupled to the housing, the cap enclosing the applicator when detachably coupled to the housing.

* * * * *